United States Patent [19]

Rovnyak

[11] 4,254,267
[45] Mar. 3, 1981

[54] MERCAPTOACYLDIHYDROPYRAZOLE CARBOXYLIC ACID DERIVATIVES

[75] Inventor: George C. Rovnyak, Hopewell, N.J.

[73] Assignee: E. R. Squibb & Sons, Inc., Princeton, N.J.

[21] Appl. No.: 88,425

[22] Filed: Oct. 25, 1979

[51] Int. Cl.³ ............... C07D 401/04; C07D 405/04; C07D 409/04
[52] U.S. Cl. .................... 548/379; 546/279; 424/263; 424/273 P
[58] Field of Search ............... 548/379; 546/279

[56] References Cited

U.S. PATENT DOCUMENTS 4,105,776  8/1978  Ondetti et al. ............ 424/274
4,211,786  7/1980  Rovnyak ................... 548/379

FOREIGN PATENT DOCUMENTS 861454 8/1978 Belgium .

Primary Examiner—Henry R. Jiles
Assistant Examiner—Natalie Harkaway
Attorney, Agent, or Firm—Lawrence S. Levinson; Donald J. Barrack

[57] ABSTRACT

Hypotensive activity is exhibited by compounds having the formula

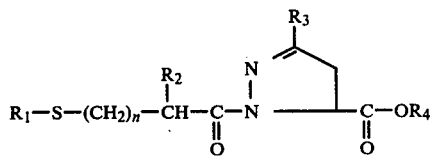

wherein:
R₁ is hydrogen, alkyl, aryl, arylalkyl or

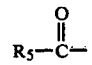

wherein R₅ is alkyl or aryl;
R₂ is hydrogen, alkyl, or haloalkyl;
R₃ is furanyl, thienyl or pyridyl;
R₄ is hydrogen, alkyl or arylalkyl; and
n is 0, 1 or 2.

8 Claims, No Drawings

MERCAPTOACYLDIHYDROPYRAZOLE CARBOXYLIC ACID DERIVATIVES

RELATED APPLICATIONS

U.S. patent application Ser. No. 18,547, filed Mar. 8, 1979, describes a group of mercaptoacylpyrazolidinone carboxylic acid derivatives having the formula

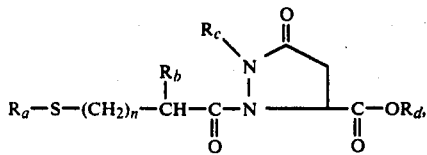

and basic salts thereof, wherein $R_a$ is hydrogen, alkyl, aryl, arylalkyl or

wherein $R_e$ is alkyl or aryl; $R_b$ is hydrogen or alkyl; $R_c$ is hydrogen, alkyl, aryl or arylalkyl; $R_d$ is hydrogen, alkyl, or arylalkyl; and n is 0, 1 or 2. The term "aryl" as used in the application is defined as phenyl or phenyl substituted with one, two, or three halogen, alkyl, alkoxy, hydroxy,

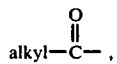

nitro, amino, alkylamino, dialkylamino, trifluoromethyl, cyano or carboxyl groups.

U.S. patent application Ser. No. 18,548, filed Mar. 8, 1979, describes a group of mercaptoacyldihydropyrazole carboxylic acid derivatives having the formula

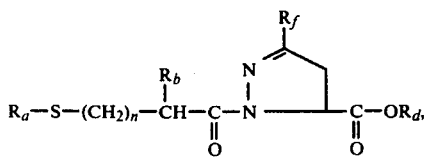

and basic salts thereof, wherein $R_a$, $R_b$, $R_d$ and n are as defined above and $R_f$ is aryl. The term "aryl" as used in the application has the same definition as set forth above.

BACKGROUND OF THE INVENTION

U.S. patent No. 4,105,776, issued Aug. 8, 1978, describes a group of thioalkanoyl derivatives of azetidine-, pyrrolidine- and piperidinecarboxylic acid compounds having the structural formula

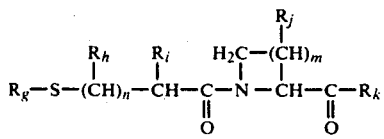

wherein the symbols can be, inter alia, as follows: $R_g$ can be hydrogen, lower alkyl, phenyl, substituted phenyl, phenyl-lower alkyl,

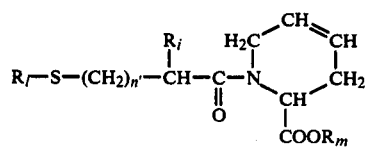

$R_h$ can be hydrogen, $R_i$ can be hydrogen or lower alkyl, $R_j$ can be hydrogen, hydroxy or lower alkyl, $R_k$ can be hydroxy, $-NH_2$ or lower alkoxy, n can be 0, 1 or 2 and m can be 1, 2 or 3.

U.S. Pat. No. 4,129,566, issued Dec. 12, 1978, describes derivatives of dehydrocyclicimino acids having the structural formula

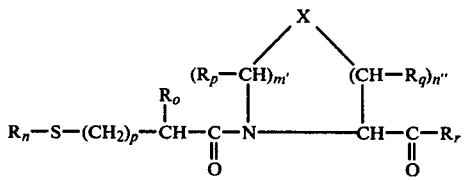

wherein the symbols can be, inter alia, as follows: $R_i$, $R_l$ and $R_m$ can each be hydrogen or lower alkyl and $n'$ can be 0 or 1.

Belgian Pat. No. 861,454, published June 2, 1978, describes compounds having the structural formula

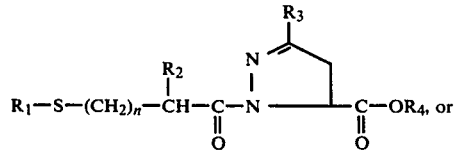

wherein the symbols can be, inter alia as follows: $R_n$ can be hydrogen, lower alkanoyl or benzoyl, $R_o$, $R_p$ and $R_q$ can each be hydrogen or lower alkyl, $R_r$ can be hydroxy or lower alkoxy, $m'$ can be 1, 2 or 3, $n''$ can be 0, 1 or 2 and $M'+n''$ can be 2 or 3, p can be 0 or 1 and X can be O, S, SO or $SO_2$, $m'$ being 2 and $n''$ being 1 when X is O.

The compounds set forth above are useful as inhibitors of the conversion of the decapeptide angiotensin I to angiotensin II, and are, therefore, useful in reducing or relieving angiotensin related hypertension.

BRIEF DESCRIPTION OF THE INVENTION

Compounds having the formula

and basic salts thereof, have hypotensive activity. In formula I, and throughout the specification, the symbols are as defined below.

$R_1$ is hydrogen, alkyl, aryl, arylalkyl or $$R_5-\overset{O}{\underset{\|}{C}}-$$

wherein $R_5$ is alkyl or aryl;

$R_2$ is hydrogen, alkyl or haloalkyl;

$R_3$ is 2-furanyl, 3-furanyl, 2-thienyl, 3-thienyl, 2-pyridyl, 3-pyridyl, 4-pyridyl or any of the aforementioned groups substituted with one or two halogen or alkyl groups.

$R_4$ is hydrogen, alkyl or arylalkyl; and n is 0, 1 or 2.

The term "aryl", as used throughout the specification either by itself or as part of a larger group, refers to phenyl or phenyl substituted with one, two or three halogen, alkyl, alkoxy, hydroxy,

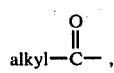

nitro, amino, alkylamino, dialkylamino, trifluoromethyl, cyano or carboxyl groups. Phenyl is the preferred aryl group.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are chlorine and bromine, except in the case of "haloalkyl" where fluorine is the preferred "halo" group. Trifluoromethyl is the preferred haloalkyl group.

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of the compounds of this invention, angiotensin dependent hypertension in the species of mammal suffering therefrom is alleviated. A single dose, or preferably two to four divided daily doses, provided on a basis of about 0.1 to 100 mg. per kilogram or body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 300 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions of suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention wherein $R_2$ is hydrogen or alkyl (this subgenus being referred to hereinafter as $R_2'$) can be obtained by reacting a 4,5-dihydro-3-heterocyclic-1H-pyrazole-5-carboxylic acid having the formula

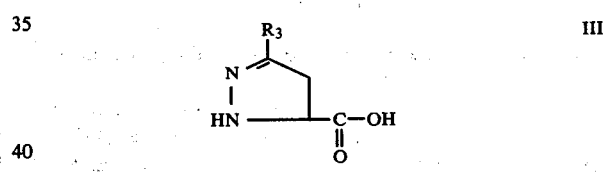

with a mercaptoacyl halide having the formula

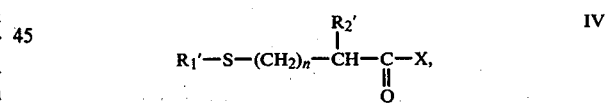

wherein $R_1'$ is a hydrolyzable protecting group and X is chlorine or bromine, to obtain the corresponding products of formula I wherein $R_1$ is other than hydrogen, $R_2$ is hydrogen or alkyl and $R_4$ is hydrogen, i.e., compounds having the formula

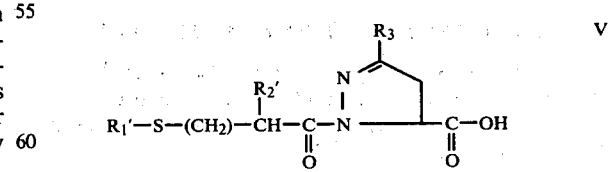

The reaction is preferably run in a two phase solvent system such as water/ether or water/ethyl acetate, in the presence of a base such as an alkali metal hydroxide or alkali metal carbonate. While reaction conditions are not critical, more favorable yields will be obtained if the reaction is run within the following parameters. The ratio of pyrazole derivative (formula III) to mercaptoacyl halide (formula IV) will preferably be within the range of 1:1 to 1:2, most preferably within the range of 1:1 to 1:1.2. The temperature of the reaction is preferably maintained at about 0°–25° C., most preferably 0°–5° C. Additional base should be added as needed to maintain the pH of the reaction mixture between about 7.0 and 8.5.

Alternatively, a 4,5-dihydro-3-heterocyclic-1$\underline{H}$-pyrazole-5-carboxylic acid of formula III can be reacted with a mixed anhydride in place of the mercaptoacyl halide of formula IV to obtain the corresponding product of formula V.

The compounds of formula I wherein $R_1$ and $R_4$ are both hydrogen can be prepared by deacylation of the corresponding compounds of formula V wherein $R_1'$ is

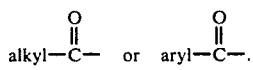

Hydrolysis of the thioacyl group can be accomplished by treatment with aqueous base, e.g., ammonium hydroxide or an alkali metal hydroxide.

The compounds of this invention wherein $R_2$ is haloalkyl (this subgenus being referred to hereinafter as $R_2''$) can be obtained by reacting a carboxylic ester of a 4,5-dihydro-3-heterocyclic-1$\underline{H}$-pyrazole-5-carboxylic acid of formula III with a thioacid derivative having the formula

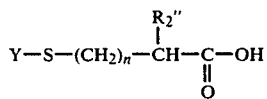

wherein Y is a protecting group. Cleavage of the sulfur protecting group and conversion of the acid ester to the corresponding acid can be accomplished using anisole, trifluoroacetic acid and mercuric acetate. The specifics of the conversion are set forth in the examples presented hereinafter.

The compounds of formula I wherein $R_4$ is alkyl or arylalkyl can be obtained by treating the corresponding acids of formula I with the appropriate diazoalkane or with the appropriate alcohol in the presence of a dehydrating agent such as dicyclohexylcarbodiimide. Alternatively, an acid of formula I can be converted first to an acid halide and then reacted with the appropriate alcohol in the presence of an acid acceptor, e.g., an organic base such as triethylamine.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The 4,5-dihydro-3-heterocyclic-1$\underline{H}$-pyrazole-5-carboxylic acids of formula III wherein $R_3$ is other than pyridyl, can be prepared using the procedure described in Ann. Pharm. Fr., 36, 67 (1978). As described therein, an acrylic acid derivative can be treated with one equivalent each of hydrazine and potassium hydroxide in aqueous ethanol at reflux for two hours, followed by acidification to obtain a starting compound of formula III. In some cases, anhydrous methanol is superior to aqueous ethanol as the reaction medium. The acrylic acid derivatives required in the preparation can be obtained by reacting glyoxylic acid with the appropriate ketone having the formula

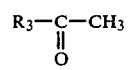

To prepare the 4,5-dihydro-3-heterocyclic-1$\underline{H}$-pyrazole-5-carboxylic acids of formula III wherein $R_3$ is pyridyl, an acetyl pyridine (2-,3-, or 4-, optionally substituted with one or two halogen or alkyl groups) is α-brominated to yield the corresponding bromomethyl pyridyl ketone. An exemplary procedure for the bromination is given in J. Org. Chem., 24, 872 (1959). Reaction of a bromomethyl pyridyl ketone with the appropriate Wittig reagent yields an acrylic acid methyl ester derivative having the formula

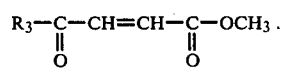

An exemplary procedure for the reaction is given in Chem. Ber., 96, 465 (1963). Hydrolysis of a methyl ester of formula VIII yields the corresponding acrylic acid derivative which can be reacted with hydrazine and potassium hydroxide in aqueous ethanol (as described above) to yield a 4,5-dehydro-3-heterocyclic-1$\underline{H}$-pyrazole-5-carboxylic acid of formula III.

The mercaptoacyl halide derivatives of formula IV and VI are prepared by methods known in the art; see, for example, Arkiv. Kimi. Mineral. Geol., 14A (7), 1940; J. Chem. Soc. 2016 (1970); J.A.C.S., 69, 2328 (1947); and J.A.C.S., 69, 2334 (1947); J. Med. Chem., 7, 3 (1964); and J. Chem. Soc., 1371 (1954).

The compounds of formula I each contains at least one asymmetric carbon and accordingly exists in stereoisomeric forms or in racemic mixtures thereof. The above described synthesis can utilize the racemate or one of the enantiomers as starting material. When the racemic starting material is used in the synthetic procedure, the stereoisomers obtained in the product can be separated by conventional fractional crystallization of the diastereomeric salt mixture formed, e.g., with an optically active amine. It is theorized that the activity of the racemic products is due mostly to the L-isomer with respect to the carbon of the amino acid, and this isomer is accordingly preferred.

The following examples are specific embodiments of this invention.

EXAMPLE 1

(±)-3-(2-Furanyl)-4,5-dihydro-1-(3-mercapto-1-oxopropyl)-1$\underline{H}$-pyrazole-5-carboxylic acid (A) 4-(2-Furanyl)-4-oxo-2-butenoic acid A mixture of 14.8 g of glyoxylic acid (in 18.5 cc of water) and 22 g of 2-acetylfuran is heated at 125°–135° C. for about 5 hours; the water is removed as it forms via a Dean Stark tube. The mass cyrstallizes over about a 16 hour period and is dissolved in 600 cc of ethyl acetate and extracted into 600 cc of 10% sodium carbonate. The aqueous solution is treated with activated charcoal and a filter aid, and then filtered. It is made strongly acid with 20% HCl and the solid which precipitates is extracted with ethyl acetate. The ethyl acetate is dried over $MgSO_4$ and removed to yield a solid residue which is dissolved in 100 cc hot acetonitrile and allowed to cool for about 16 hours. The solid is filtered to yield 7.2 g of the title compound, melting point 153°–155° C.

(B)
(±)-3-(2-Furanyl)-4,5-dihydro-1H-pyrazole-5-carboxylic acid

Potassium hydroxide (660 mg) is dissolved in 25 cc of methanol and 1.66 g of 4-(2-furanyl)-4-oxo-2-butenoic acid is added. Hydrazine (320 mg) is then added and the solution is refluxed for 2 hours. The methanol is removed and the viscous residue is dissolved in 50 cc of water. The solution is made strongly acid with 20% HCl and a precipitate forms. The solid is filtered quickly to yield 1.2 g of the title compound, melting point 185°–190° C., dec.

(C)
(±)-1-[3-(Acetylthio)-1-oxopropyl]-3-(2-furanyl)-4,5-dihydro-1H-pyrazole-5-carboxylic acid (±)-3-(2-Furanyl)-4,5-dihydro-1H-pyrazole-5-carboxylic acid (4.5 g) is dissolved in 200 cc of water containing 1.38 g of sodium carbonate (pH 9.4) at 10° C. 3-(Acetylthio)propionyl chloride (4.15 g) and 20% sodium carbonate solution are added simultaneously maintaining the pH between 8.5 and 9.4 and the temperature at 10° C. The final reaction mixture (pH 9.7) is stirred at room temperature for 2 hours and extracted with ethyl acetate (discarded) and the aqueous layer made strongly acid with 20% HCl. A precipitate forms which is extracted into ethyl acetate immediately. The solvent is dried and removed to yield 4.5 g of crystalline material which cannot be recrystallized.

(D)
(±)-3-(2-Furanyl)-4,5-dihydro-1-(3-mercapto-1-oxopropyl)-1H-pyrazole-5-carboxylic acid Aqueous ammonia (12 cc) is stirred under nitrogen at 10° C. for 30 minutes, at which point 4.3 g of (±)-1-[3-(acetylthio)-1-oxopropyl]-3-(2-furanyl)-4,5-dihydro-1H-pyrazole-5-carboxylic acid is added. The resulting solution is stirred for about 2.5 hours under nitrogen. The solution is extracted with ethyl acetate (discarded) and then made strongly acid with 20% HCl. An oil results which is extracted with 150 cc ethyl acetate. The aqueous layer is extracted with an additional two 150 cc portions of ethyl acetate. The combined organic layers are extracted with 200 cc saturated NaCl and then dried over $MgSO_4$. The solvent is removed to yield 3.7 g of semicrystalline residue which is triturated with ether to yield 2.3 g of product melting at 121°–123° C. The product does not crystallize readily from any solvent tried.

Analysis calc'd for $C_{11}H_{12}N_2O_4S$: N, 10.44; C, 49.24; H, 4.51; S, 11.95; SH, 100%. Found: N, 10.14; C, 49.39; H, 4.59; S, 11.43; SH, 99%.

EXAMPLE 2

(±)-4,5-Dihydro-1-(3-mercapto-1-oxopropyl)-3-(2-thienyl)-1H-pyrazole-5-carboxylic acid (A) 4-(2-Thienyl)-4-oxocrotonic acid A two phase mixture of 18 grams glyoxylic acid (an 80% solution of glyoxylic acid in water) and 25.2 grams of 2-acetylthiophene is heated to 125° C. with stirring, and heating and stirring are maintained for about 5 hours. A clear solution forms at 115° C. and the water formed is removed by means of a Dean-Stark apparatus. On cooling the residue solidifies. It is dissolved in 100 cc ether and extracted with 150 cc of a 20% solution of $Na_2CO_3$. This aqueous solution is treated with activated charcoal, filtered and made strongly acid with 20% HCl. The solid is filtered and dissolved in about 1 L ether. The ether is dried over $MgSO_4$ and removed to yield 19.1 g of the title compound, melting point 139°–142° C.

(B)
(±)-4,5-Dihydro-3-(2-thienyl)-1H-pyrazole-5-carboxylic acid

Potassium hydroxide (3.3 g) is dissolved in 100 cc of methanol and 9.1 g of 4-(2-thienyl)-4-oxocrotonic acid is added. To the resulting solution is added 2 g of hydrazine and the solution is refluxed for 2 hours. The methanol is removed and the viscous residue dissolved in 80 cc of water. The solution is made strongly acid with 20% HCl and a precipitate forms. It is filtered and air-dried to yield 8.1 g of the title compound, melting point 163°–165° C., dec. After recrystallization from ethanol the compound is constant melting at 171°–173° C., dec.

(C)
(±)-1-[3-(Acetylthio)-1-oxopropyl]-4,5-dihydro-3-(2-thienyl)-1H-pyrazole-5-carboxylic acid (±)-4,5-Dihydro-3-(2-thienyl)-1H-pyrazole-5-carboxylic acid is dissolved in aqueous $Na_2CO_3$ (1.38 g) at pH 8.6. The temperature is lowered to 5° C. and 3-(acetylthio)propionyl chloride (4.15 g) and a 25% solution of $Na_2CO_3$ are added simultaneously maintaining the pH at 8–9. The final pH is 8.9 and the reaction is stirred for 2 hours at room temperature. It is then extracted with ethyl acetate and the ethyl acetate is discarded. The aqueous layer is made strongly acid with 20% HCl and the gummy precipitate is extracted with ethyl acetate. The ethyl acetate is dried over $MgSO_4$ and removed to yield a viscous residue (7.2 g) which is triturated with ether to yield 5.1 g of material, melting point 127°–130° C., dec. After recrystallization from $CH_3CN$ (very soluble) the melting point is constant at 134°–136° C., dec.

(D)
(±)-4,6-Dihydro-1-(3-mercapto-1-oxopropyl)-3-(2-thienyl)-1H-pyrazole-5-carboxylic acid (±)-1-[3-(Acetylthio)-1-oxopropyl]-4,5-dihydro-3-(2-thienyl)-1H-pyrazole-5-carboxylic acid (4.7 g) is added to a cooled solution of aqueous ammonia (12 cc) and stirred at 10° C. under nitrogen for 2 hours. A clear solution forms after about 10 minutes stirring. The aqueous layer is washed with ethyl acetate (discarded) and the aqueous layer made strongly acid with 20% HCl in the presence of ethyl acetate. The aqueous layer is extracted with two add'l 150 cc portions of ethyl acetate and the combined organic layers dried over $MgSO_4$.

The solvent is removed yielding 3.2 g of product, melting point 138°–140° C.

Analysis calc'd for $C_{11}H_{12}N_2O_3S_2$: N, 9.85; C, 46.46; H, 4.26; S, 22.55; SH 100%. Found: N, 9.65; C, 46.79; H, 4.34; S, 22.35; SH, 99.9%.

EXAMPLE 3

(±)-3-(2-Thienyl)-4,5-dihydro-1-[D,L-3,3,3-trifluoro-2-(mercaptomethyl)-1-oxopropyl]-1H-pyrazole-5-carboxylic acid

(A)

D,L-[3,3,3-Trifluoro-2-[4-(methoxy)benzylthiomethyl]]propionic acid

A heat mixture of 3.9 g of 2-(trifluoromethyl) acrylic acid [prepared according to the procedures described in J. Med. Chem., 7, 3 (1964) and J. Chem. Soc., 1371 (1954)] and 4.3 g of 4-methoxybenzylthiol is stirred at 100°–110° C. for one hour. The mixture solidifies at room temperature. Recrystallization from cyclohexane affords 6.8 g of the title compound, melting point 72°–74° C.

(B)

(±)-4,5-Dihydro-1-(benzyloxycarbonyl)-3-(2-thienyl)-1H-pyrazole-5-carboxylic acid To a stirred mixture of 9.8 g of (±)-4,5-dihydro-3-(2-thienyl)-1H-pyrazole-5-carboxylic acid (see example 2B) and 13.8 g of potassium carbonate in 80 ml of water and 40 ml of acetone there is added slowly 9.3 g of benzyl chloroformate dissolved in 50 ml of acetone, maintaining the temperature of the mixture at 10°–15° C. with an ice bath. After stirring at room temperature for 2 hours, the mixture is diluted with an equal volume of water and washed twice with ether. The aqueous layer containing some solids, is adjusted to pH 3.0 with 6 N HCl and cooled and filtered to obtain the title compound.

(C)

(±)-4,5-Dihydro-1-(benzyloxycarbonyl)-3-(2-thienyl)-1H-pyrazole-5-carboxylic acid, t-butyl ester A mixture of 6.6 g of (±)-4,5-dihydro-1-(benzyloxycarbonyl)-3-(2-thienyl)-1H-pyrazole-5-carboxylic acid, 5 ml of isobutylene, 25 ml of ether and 0.25 ml of concentrated sulfuric acid is shaken in a pressure vessel for about 16 hours. The reaction vessel is vented (−10° C.) and the contents are washed with ice cold aqueous sodium hydroxide. The organic fraction is dried over anhydrous magnesium sulfate and concentrated in vacuo to give the title compound.

(D)

(±)-4,5-Dihydro-3-(2-thienyl)-1H-pyrazole-5-carboxylic acid, t-butyl ester

A solution of 5.0 g of (±)-4,5-dihydro-1-(benzyloxycarbonyl)-3-(2-thienyl)-1H-pyrazole-5-carboxylic acid, t-butyl ester in 75 ml of ethanol containing 0.5 g of 5% palladium on carbon is hydrogenated at atmospheric pressure until the uptake of hydrogen ceases. The catalyst is removed by filtration through Celite and the filtrate is concentrated in vacuo to yield the title compound.

(E)

(±)-3-(2-Thienyl)-4,5-dihydro-1-[3,3,3-trifluoro-2-[4-(methoxy)benzylthiomethyl]-1-oxopropyl]-1H-pyrazole-5-carboxylic acid, t-butyl ester A mixture of 2.94 g of D,L-[3,3,3-trifluoro-2[4-(methoxy)benzylthiomethyl]]propionic acid and 2.52 g of (±)-4,5-dihydro-3-(2-thienyl)-1H pyrazole-5-carboxylic acid, t-butyl ester in 500 ml of dichloromethane is stirred at 0° C. and treated with 2.06 g of dicyclohexyl carbodiimide. After 30 minutes the cooling bath is removed and stirring is continued at ambient temperature for about 16 hours. Solids are removed by filtration and the filtrate is washed with 5% sodium bicarbonate, 5% potassium disulfate and saturated brine and dried over anhydrous magnesium sulfate. Removal of solvent affords the title compound.

(F)

(±)-3-(2-Thienyl)-4,5-dihydro-1-[D,L-3,3,3-trifluoro-2-(mercaptomethyl)-1-oxopropyl]-1H-pyrazole-5-carboxylic acid A solution of 3.6 g of (±)-3-(2-thienyl)-4,5-dihydro-1-[3,3,3-trifluoro-2-[4-(methoxy)benzylthiomethyl]-1-oxopropyl]-1H-pyrazole-5-carboxylic acid t-butyl ester and 10 ml of anisole is cooled to 0° C. in an ice bath and 100 ml of trifluoroacetic acid is added, followed by 2.3 g of mercuric acetate. The bath is removed and the mixture is stirred at ambient temperature for one hour. After concentration in vacuo, the residue is triturated with ether/pentane and the solid obtained is suspended in water and saturated with hydrogen sulfide gas (10 minutes). The resulting solid in suspension is removed by filtration through Celite. Lyophilization gives the product.

EXAMPLE 4

(±)-3-(2-Pyridyl)-4,5-dihydro-1-(3-mercapto-1-oxopropyl)-1H-pyrazole-5-carboxylic acid

(A) 4-(2-Pyridyl)-4-oxo-2-butenoic acid, methyl ester

A solution of 33.4 g of carbomethoxymethylene triphenylphosphine [Helv. Chim. Acta. 40, 1242 (1957)] in 500 ml of dry benzene under nitrogen is treated with 10 g of 2-(bromoacetyl)pyridine and heated at reflux temperature for 2 hours. The reaction mixture is cooled and filtered to remove carbomethoxymethyl triphenylphosphonium bromide. The filtrate, containing triphenylphosphine, is treated with methyl bromoacetate and heated at reflux temperature for 2 hours. Cooling and filtration removes additional phosphonium salt. The filtrate is concentrated in vacuo yielding the title compound.

(B) 4-(2-Pyridyl)-4-oxo-2-butenoic acid

A mixture of 15 g of 4-(2-pyridyl)-4-oxo-2-butenoic acid, methyl ester in chloroform (50 ml) is stirred with 3.14 g of sodium hydroxide in 50 ml of water for 5 hours at room temperature. The aqueous layer is separated, washed with chloroform and acidified with 4.71 g of acetic acid, yielding the title compound.

(C)

(±)-3-(2-Pyridyl)-4,5-dihydro-1H-pyrazole-5-carboxylic acid

Potassium hydroxide (3.29 g) is dissolved in 250 ml of methanol and 8.85 g of 4-(2-pyridyl)-4-oxo-2-butenoic acid is added. Hydrazine (1.6 g) is then added and the solution is heated at reflux temperature for 5 hours. Solvent is removed in vacuo and the residue is dissolved in 50 ml of water and treated with 3.0 g of acetic acid yielding the title compound.

(D)

(±)-1-[3-(Acetylthio)-1-oxopropyl]-3-(2-pyridyl)-4,5-dihydro-1H-pyrazole-5-carboxylic acid (±)-3-(2-Pyridyl)-4,5-dihydro-1H-pyrazole-5-carsulfate and concentrated in vacuo to yield the title compound.

EXAMPLES 5–8

Following the procedure of Example 1, parts A, B and C, but substituting the compound of column I for 2-acetylfuran and the acid chloride derivative of column II for 3-(acetylthio)propionyl chloride, yields the compound of column III.

| Column I | Column II | Column III |
| --- | --- | --- |
| 5. 2-acetyl-3-methylthiophene | 3-(acetylthio)-2-ethyl-propionyl chloride | (±)-1-[3-(acetylthio)-2-ethyl-1-oxopropyl]-4,5-dihydro-3-(3-methyl-2-thienyl)-1H-pyrazole-5-carboxylic acid |
| 6. 2-acetyl-5-chlorothiophene | 3-(benzoylthio)-2-methylpropionyl chloride | (±)-1-[3-(benzoylthio)-2-methyl-1-oxopropyl]-3-(5-chloro-2-thienyl)-4,5-dihydro-1H-pyrazole-5-carboxylic acid |
| 7. 2-acetyl-5-methylfuran | 3,3,3-trifluoro-2-[4-(methoxy)benzyl-thiomethyl]propionyl chloride | (±)-1-[3,3,3-trifluoro-2-[4-(methoxy)benzylthiomethyl]-4,5-dihydro-3-(5-methyl-2-furanyl)-1H-pyrazole-5-carboxylic acid |
| 8. 2-bromo-3-acetylfuran | 3-(acetylthio)-2-methyl-propionyl chloride | (±)-1-[3-(acetylthio)-2-methyl-1-oxopropyl]-3-(2-bromo-3-furanyl)-4,5-dihydro-1H-pyrazole-5-carboxylic acid | boxylic acid (3.82 g) is dissolved in 100 ml of water containing 2.12 g of sodium bicarbonate at 10° C. 3-(Acetylthio)propionyl chloride (3.9 g) in 15 ml of ether and 20% sodium carbonate solution are added simultaneously; the pH is maintained between 7.5 and 8.5. The reaction mixture is then stirred at room temperature for 2 hours and extracted with ether (discarded). The aque-

EXAMPLES 9–12

Following the procedure of Example 4, but substituting the compound of column I for 2-(bromoacetyl)pyridine and the compound of column II for 3-(acetylthio)propionyl chloride, yields the compound of column III.

| Column I | Column II | Column III |
| --- | --- | --- |
| 9. 3-(bromoacetyl)pyridine | 3-(acetylthio)-2-methyl-propionyl chloride | (±)-4,5-dihydro-1-(3-mercapto-2-methyl-1-oxopropyl)-3-(3-pyridyl)-1H-pyrazole-5-carboxylic acid |
| 10. 4-(bromoacetyl)pyridine | 3-(benzylthio)-2-ethyl-propionyl chloride | (±)-4,5-dihydro-1-(2-ethyl-3-mercapto-1-oxopropyl)-3-(4-pyridyl)-1H-pyrazole-5-carboxylic acid |
| 11. 2-bromoacetyl-4-methyl-pyridene | (acetylthio)acetyl chloride | (±)-4,5-dihydro-1-(2-mercapto-1-oxoethyl)-3-(4-methyl-2-pyridyl)-1H-pyrazole-5-carboxylic acid |
| 12. 2-bromoacetyl-4-chloro-pyridine | 4-(acetylthio)butyryl chloride | (±)-3-(4-chloro-2-pyridyl)-4,5-dihydro-1-(4-mercapto-1-oxobutyl)-1H-pyrazole-5-carboxylic acid | ous layer is acidified with acetic acid and extracted with ethyl acetate three times. The solvent is dried over anhydrous magnesium sulfate and concentrated in vacuo, yielding the title compound.

(E)

(±)-3-(2-Pyridyl)-4,5-dihydro-1-(3-mercapto-1-oxopropyl)-1H-pyrazole-5-carboxylic acid Aqueous ammonia (12 ml of 7 N) is stirred at 0°–5° C. under argon and 3.5 g of (±)-1-[3-(acetylthio)-1-oxopropyl]-3-(2-pyridyl)-4,5-dihydro-1H-pyrazole-5-carboxylic acid is added. The resulting solution is stirred for 2 hours under argon and is then extracted with ethyl acetate (discarded). The aqueous layer is acidified with acetic acid and extracted with ethyl acetate (three 50 ml portions). The combined organic layers are washed with saturated brine, dried over anhydrous magnesium

What is claimed is:

1. A compound having the formula

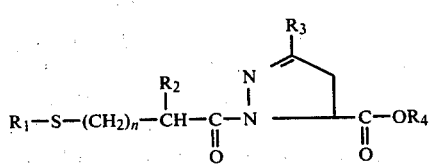

or a basic salt thereof, wherein:

$R_1$ is hydrogen, alkyl, aryl, arylalkyl or

wherein R$_5$ is alkyl or aryl;
R$_2$ is hydrogen, alkyl or haloalkyl;
R$_3$ is 2-furanyl, 3-furanyl, 2-thienyl, 3-thienyl, 2-pyridyl, 3-pyridyl, 4-pyridyl or any of the aforementioned groups substituted with one or two halogens or alkyl groups;
R$_4$ is hydrogen, alkyl or arylalkyl; and
n is 0, 1 or 2; wherein the term "aryl", as used by itself or as part of a larger group, refers to phenyl or phenyl substituted with one, two or three halogen, alkyl, alkoxy, hydroxy,

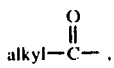

nitro, amino, alkylamino, dialkylamino, trifluoromethyl, cyano or carboxyl groups, and the terms "alkyl" and "alkoxy", as used individually or as part of a larger group, refer to groups having 1 to 8 carbon atoms.

2. A compound in accordance with claim 1 wherein R$_1$ is hydrogen, alkyl, aryl, arylalkyl or

wherein R$_5$ is alkyl or aryl.

3. A compound in accordance with claim 2 wherein R$_2$ is hydrogen, methyl or trifluoromethyl.

4. A compound in accordance with claim 1 wherein R$_1$ is hydrogen.

5. A compound in accordance with claim 1 wherein n is 1.

6. A compound in accordance with claim 1 wherein R$_3$ is 2-furanyl or 2-thienyl.

7. The compound in accordance with claim 1, (±)-3-(2-furanyl)-4,5-dihydro-1-(3-mercapto-1-oxopropyl)-1H-pyrazole-5-carboxylic acid.

8. The compound in accordance with claim 1, (±)-4,5-dihydro-1-(3-mercapto-1-oxopropyl)-3-(2-thienyl)-1H-pyrazole-5-carboxylic acid.

* * * * *

UNITED STATES PATENT AND TRADEMARK OFFICE
CERTIFICATE OF CORRECTION

PATENT NO. : 4,254,267
DATED : March 3, 1981
INVENTOR(S) : Geroge C. Rovnyak

It is certified that error appears in the above-identified patent and that said Letters Patent are hereby corrected as shown below:

Column 3, line 59, "or" should read --of--

Column 4, line 19, "of" should read --or--

Column 6, line 34, "dihydro" is misspelled

Column 6, rewrite line 36 to read --The derivatives of formulas IV and VI are prepared by methods known in the art;--

Column 6, line 67, "crystallizes" is misspelled

Column 9, line 16, "neat" is misspelled

In the table bridging columns 11 and 12, example 11, column I, "pyridine" is misspelled Column 13, line 10, "halogen" is misspelled Signed and Sealed this Twenty-ninth Day of September 1981

[SEAL]

Attest:

Attesting Officer

GERALD J. MOSSINGHOFF

Commissioner of Patents and Trademarks